(12) United States Patent
Hunter et al.

(10) Patent No.: US 7,625,350 B2
(45) Date of Patent: Dec. 1, 2009

(54) GLIDE SLEEVE BRACE

(75) Inventors: David Hunter, Chestnut Hill, MA (US); Glenn Colaco, 41 Oleander Parade, Caringbah, NSW (AU) 2298

(73) Assignee: Glenn Colaco, Caringbah (AU)

( * ) Notice: Subject to any disclaimer, the term of this patent is extended or adjusted under 35 U.S.C. 154(b) by 197 days.

(21) Appl. No.: 11/446,331

(22) Filed: Jun. 3, 2006

(65) Prior Publication Data
US 2007/0282240 A1 Dec. 6, 2007

(51) Int. Cl.
*A61F 5/00* (2006.01)
*A61F 13/00* (2006.01)
*A41D 13/08* (2006.01)
*A41D 13/00* (2006.01)
*A61F 13/06* (2006.01)

(52) U.S. Cl. .............................. 602/62; 602/61; 602/60; 602/41; 602/26; 602/23; 602/5; 602/1; 2/16; 2/17; 2/18; 2/19; 2/20; 2/21; 2/22; 2/23; 2/24; 128/892; 128/889; 128/846

(58) Field of Classification Search .................... 602/23, 602/26, 62, 61, 60, 41, 5, 1; 2/16–24; 128/892, 128/889, 846
See application file for complete search history.

(56) References Cited

U.S. PATENT DOCUMENTS

| 4,084,584 | A |   | 4/1978  | Detty              |        |
|-----------|---|---|---------|--------------------|--------|
| 4,116,236 | A | * | 9/1978  | Albert             | 602/26 |
| 4,296,744 | A |   | 10/1981 | Palumbo            |        |
| 5,277,697 | A |   | 1/1994  | France et al.      |        |
| 5,613,943 | A | * | 3/1997  | Palumbo            | 602/62 |
| 5,865,776 | A | * | 2/1999  | Springs            | 602/26 |
| 6,149,616 | A | * | 11/2000 | Szlema et al.      | 602/62 |
| 2004/0153017 | A1 | * | 8/2004 | Simmons et al.    | 602/26 |
| 2006/0264793 | A1 | * | 11/2006 | Simmons et al.    | 602/23 |

OTHER PUBLICATIONS

"The Efficacy of Orthotics for Anterior Knee Pain in Military Trainees." Miller, MD; Hinkin, MD; Wisnowski, MD."American Journal of Knee Surgery." 1997 Winter; 10(1): 10-3.USA.

* cited by examiner

*Primary Examiner*—Patricia Bianco
*Assistant Examiner*—Tarla R Patel
(74) *Attorney, Agent, or Firm*—The Hill Firm; Dennis A. Gross

(57) ABSTRACT

A patellofemoral brace consisting of a sleeve adapted to be worn by a user in the knee area and having a patella interior opening is provided with a glide which is adjustably carried by the sleeve and which includes a patella engaging brace pad which may be silicon filled and which is generally U-shaped having one longer leg and one shorter leg. The brace is used to influence proper positioning of the patella by the generation of a force applied to the superolateral aspect of the patella to correct misalignment of the patella.

12 Claims, 3 Drawing Sheets

GLIDE SLEEVE BRACE

FIELD OF THE INVENTION

This invention relates to knee braces and particularly to a patellofemoral knee brace employing a sleeve and an adjustable position glide for biasing the patella.

BACKGROUND OF THE INVENTION

Patellar malalignment is known as a translational or rotational deviation of the patella in any axis that causes aberrant dispersion of the forces transmitted through the patellofemoral joint. Ideally the patella is located centrally in the trochlear groove where the imposed forces of the quadriceps and the patella tendon are properly established over the patellofemoral joint. Malalignment of the patella, laterally, medially, rotationally, vertically or any combination thereof including tilt, can adversely impact the mechanics of the patellofemoral joint and cause pain during flexion of the knee. Observation of malalignment shows lateral misalignment to be more common than medial.

It has been known to apply positioning forces to the patella to resist mispositioning, such positioning forces being applied by many different types of devices.

A common positioning technique is the use of tape applied to the skin at the patella and tensioned in a direction chosen to accommodate proper positioning of the patella. One known example is the McConnel taping technique. While such taping for patellar subluxation may reduce abnormal movement of the patella and may assist in proper positioning, proper positioning of the tape and the proper application of force vectors generated by the taping are difficult to predictably, repetitively achieve. Additionally the tape itself is discomforting, temporary and may be unduly binding of the knee joint while placing undesirable tension on the skin.

As an alternative to taping it has been known to employ various types of knee braces and supports, including sleeves received about the leg and positioned over the knee. Such sleeves can include anterior patellar openings and may include affixed pads for restricting movement of the patella. One such sleeve device is shown, for example in U.S. Pat. No. 4,084,584. In such a construction, the fixed position of the pad with respect to the sleeve requires that all adjustment of the pad for effect on the patella be through adjustment of the position of the sleeve on the leg with the action of the pad being essentially static. Attempts to apply a dynamic force may be defeated by movement of the sleeve during normal or energetic flexion of the knee joint.

It has been suggested to apply adjustable biasing means either to patella-engaging pads fixed to the sleeve adjacent the anterior opening, such as shown in U.S. Pat. No. 4,296,774 or pads which are affixed to a separate tensioning body which may be received around the sleeve, such as shown in U.S. Pat. No. 5,613,943. While such devices provide some control over the degree of force exerted by the pad on the patella, that force is generally limited to a medial force such that the ability of the bracing pad to properly align the patella is limited.

It would therefore be an advance in the art to provide a patellar alignment system or brace having a wide range of adjustability which is comfortable to wear and which can apply forces to both the lateral and superior borders of the patella. It would be a further improvement in the art to provide such a brace that is self-conforming to the patella and where the force is applied over a wider area of contact with the patella in a direction offsetting the particular misalignment experienced by the patient.

SUMMARY OF THE INVENTION

This invention provides an improved patellofemoral brace consisting of a sleeve and a glide, with the glide carrying a pad. The sleeve is a generally tubular body adapted to be slipped over the foot and positioned around the knee. It has a generally ovaloid anterior opening in a frontal portion thereof adapted to be positioned over the patella exposing the patella region and skin of the user. Preferably the sleeve is formed of an elastic material and may be at least partially provided with, at least on its undersurface, a woven or non-woven fabric-like material.

The glide of this invention consists of a generally U-shaped member having a pad at the bight and extending legs. The bight section is affixed to the sleeve adjacent the anterior opening with the pad extending over the opening edge at least at one side of the opening and along a portion of the top or bottom of the opening. To this end, the pad itself is generally U or C-shaped having one longer leg and one shorter leg whereby the inside of the bight of the same can be brought into contact with a side of the skin covered patella while the longer leg may be brought into contact with a top or bottom area of the skin covered patella. The legs of the glide can then be adjusted with respect to one another to provide force application at the patella as desired to urge the patella to a proper position. Generally the glide will be attached at the lateral side of the opening with the pad biasing lateral and superior areas of the patella to urge it medially and reduce inferior tilt.

To secure the legs of the glide to the sleeve, both the glide leg's undersurface and portions of the outersurface of the sleeve may be provided with fasteners such as hook and loop fasteners.

The pad is preferably formed of a material which will resist sliding over the skin while being yieldable, with resistance, so as to be able to provide a force vector to the patella, determined by the relative position and tensioning of the legs of the glide. Additionally the pad may be contoured, at least on its undersurface, to assist in conforming to the general shape of the force receiving surfaces of the patella whereby boundary areas of the skin covered patella may be nestled in the pad.

It is therefore an object of this invention to provide an improved patellofemoral joint brace.

It is also an object of this invention to provide a patellar alignment system that provides an alignment force that is adequate to align a wide range of patellar malalignments.

It is a further object of the invention to provide a patellar alignment system that provides an alignment system that may be easily tailorable to individual patients.

It is a further object of the invention to provide a patellar alignment system that may be easily applied and easily adjusted after application.

A further object of the invention is to provide a patellar alignment system that is stable even under the rigors present during intense exercise.

It is also an object of the invention to provide a patellar alignment system that is cost effective to manufacture and relatively simple to operate.

It is another and more particular object of the invention to provide a patellofemoral brace which is adjustable to apply selective pressure to areas of the patella to compensate for patellar malalignment.

It is another and more particular object of this invention to provide a knee brace including a sleeve received over the leg of the user in the knee joint area with a frontal opening receiving the patella, a glide member having a pressure pad carried thereby carriable by the sleeve, the glide member having tension adjusting strap members repositionably attachable to the sleeve for engaging the pad against the kneecap with patient specific force vectors applied by the pad to the kneecap to urge the kneecap towards a normal positioning.

It is a specific object of this invention to provide a brace for use at the patellofemoral joint of a human consisting of an open ended sleeve receivable over the foot of the user and positionable at the joint, the sleeve formed, at least in part, of a material resisting slippage with respect to the user's skin and being elastic to grip the user's leg to remain substantially in place thereon during flexure of the joint, the sleeve having an anterior opening therethrough positionable over the patella area, the sleeve having affixed thereto a glide including a generally yieldable resilient pad for engaging at least lateral and superior surface portions of the skin covered patella, the glide being moveably adjustable on the sleeve and including tension applying members selectively positionable and repositionably attached to the sleeve for the purpose of applying force vectors at the patella to urge the patella towards a properly aligned position at the patellofemoral joint.

These and other objects of the invention will be apparent by those of ordinary skill in the art from the following description of the preferred embodiment, it being understood that those of ordinary skill in the art will readily ascertain that the invention may be practiced in different modes employing different selected materials or variations thereof.

DESCRIPTION OF THE PREFERRED EMBODIMENT

Figure 1:
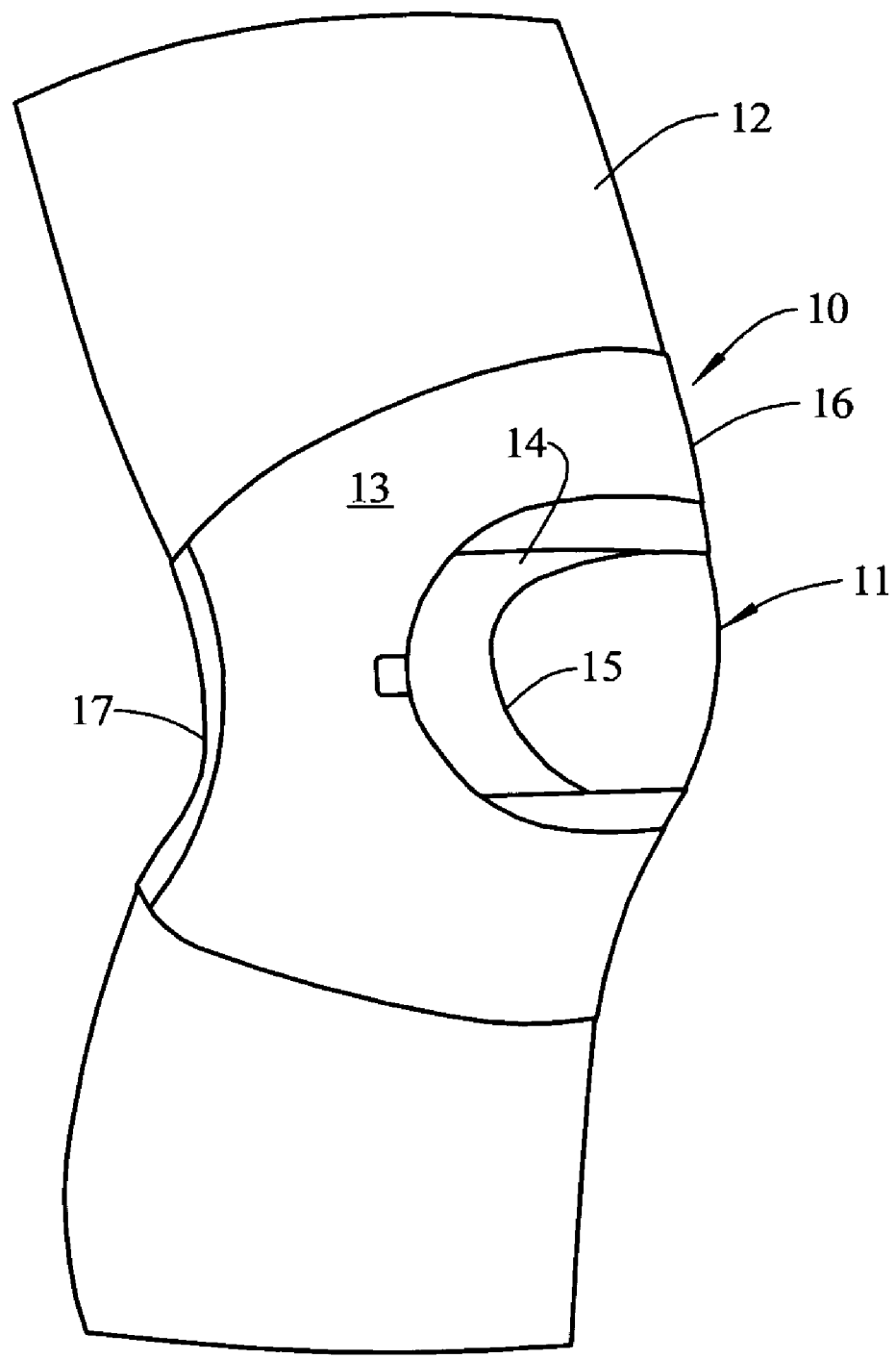
FIG. 1 is a partial view of the leg having the glide sleeve of this invention positioned at the knee.

As shown in FIG. 1, a brace 10 is received over the knee region 11 of a leg 12. The brace includes a sleeve 13, a glide 14 and a pad 15 which is contactable with the skin at an outer boundary area of the patella.

The sleeve 13 is generally tubular having a larger front face 16 which has a greater axial extent than a back portion 17. The sleeve is preferably made of resilient material that will resist slipping when positioned on the leg of the user in contact with the skin. Neoprene is a suitable material for construction of the sleeve. The sleeve, although being generally tubular, may have a somewhat constricted central section so as to conform to the general anatomical exterior shape of the leg above, below and at the knee joint.

Portions 21 of the sleeve, including at least the interior of the back surface portion 17, may be coated with, or constructed of, a woven or non-woven fibrous material to provide increased comfort and wearability and to accommodate flexure of the knee at the back side. For example, in a preferred embodiment, the interior of the back of the sleeve may be felt-lined, whereas in a further embodiment the sleeve could be constructed of two pieces utilizing a fabric portion having, preferably, elastomaric qualities woven thereinto such as is commonly found, in example, in elastic bandages and wraps. The fabric portion will then form at least part of the back portion 17 and can be attached to the remainder of the sleeve 13 in various ways such as by sewing.

Although a greater or lesser extent of the sleeve may be formed of or with a lining of woven or non-woven natural or synthetic fibrous materials, in a preferred embodiment the majority of the circumference and axial length of the sleeve is formed of a material such as Neoprene which has a tendency to frictionally engage the skin so as to resist relative movement once properly secured in place and which is elastomaric to grip the leg. This is particularly important for less sedentary patients and in particular for those who may engage in athletic activities requiring forceful knee flexion.

Figure 2:
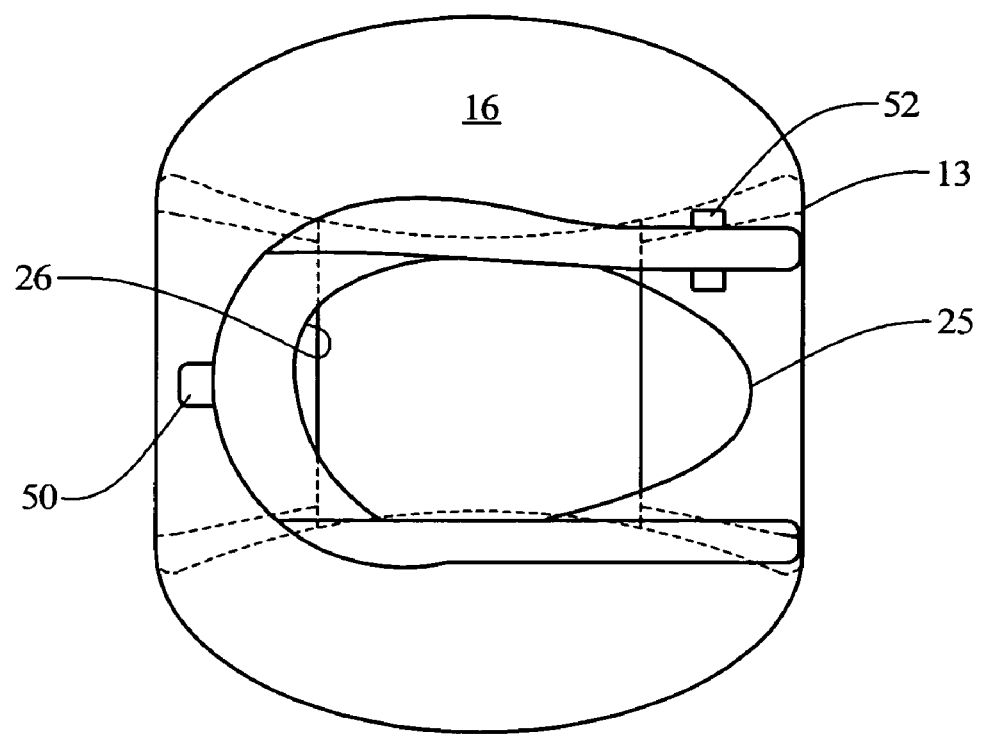
FIG. 2 is a front view of the glide sleeve of this invention showing underlying portions in dotted lines.
Figure 3:
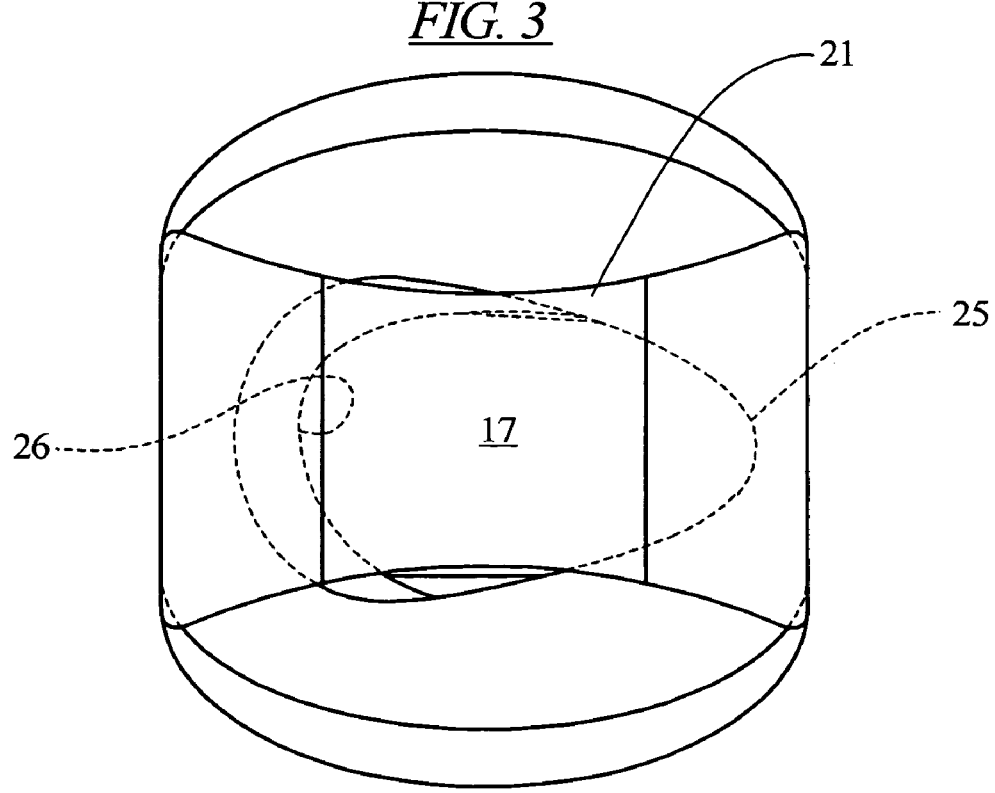
FIG. 3 is a back view of the glide sleeve of this invention showing underlying portions by dotted lines.
Figure 4:
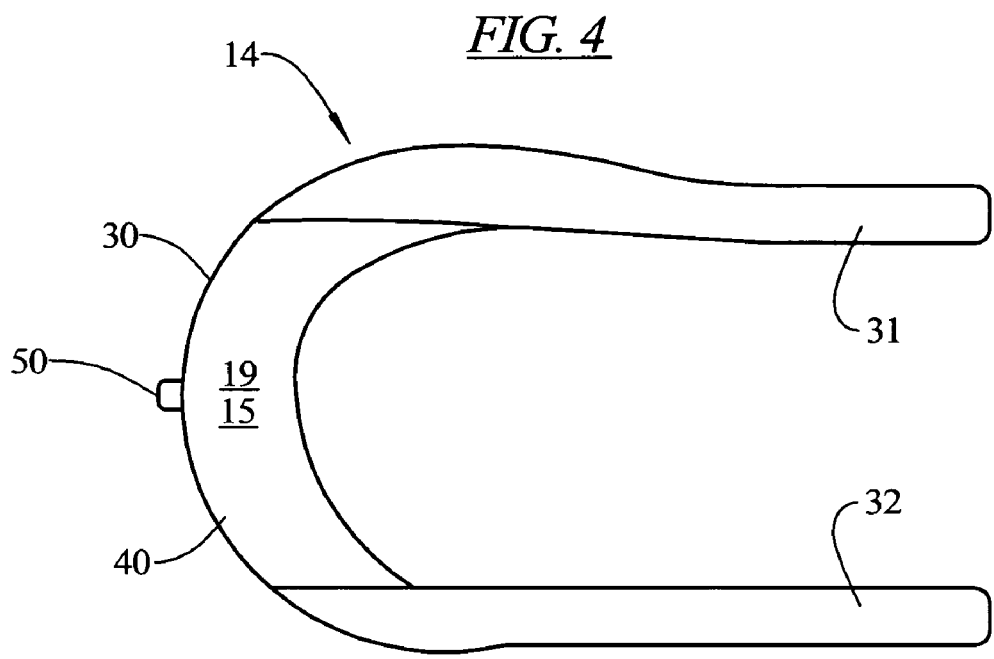
FIG. 4 is an outside view of the glide of this invention.
Figure 6:
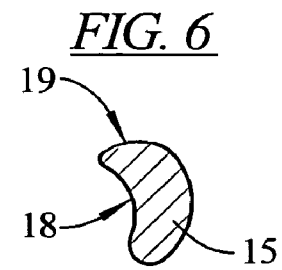
FIG. 6 is a cross section taken along the line VI-VI of FIG. 5.
Figure 5:
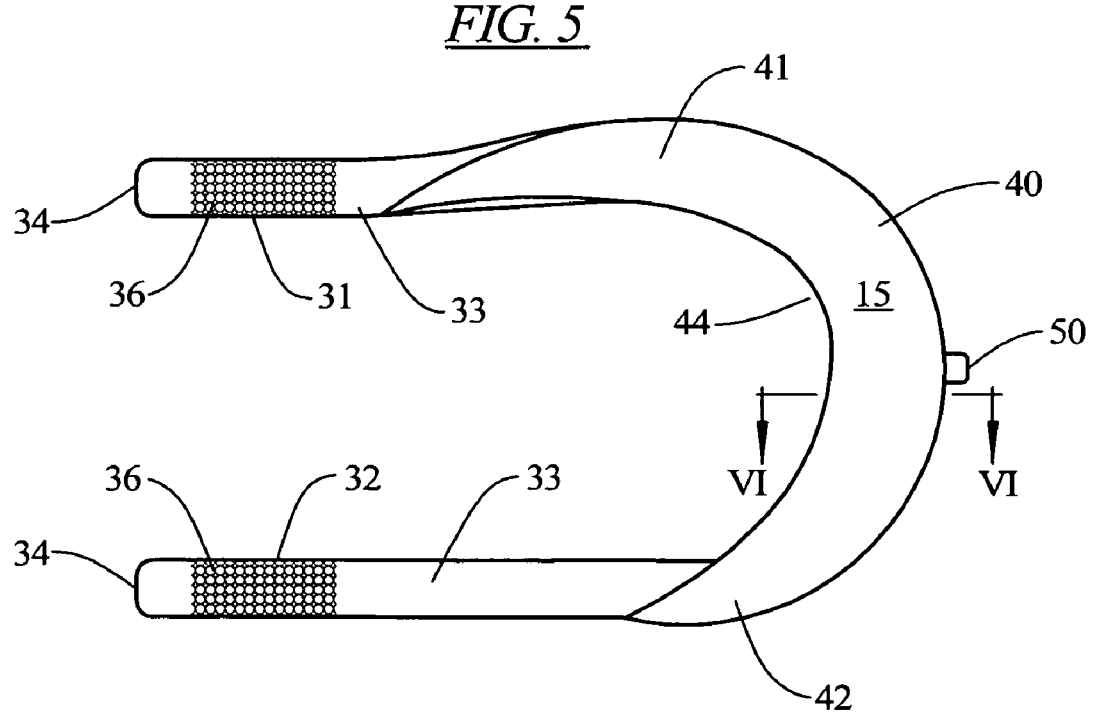
FIG. 5 is an inside view of the glide of this invention.

The front portion 16 is provided with an anterior opening 25 to expose the patella area exposing the skin covered patella through the opening. While the opening may be of any shape appropriate for such exposure, the use of an elongated opening, either oval, ovaloid or egg shaped is preferred, a generally egg shaped opening being shown in FIGS. 2 and, by dotted lines, in FIG. 3. The wider end 26 of the opening 25 is optimally positioned at the lateral side of the sleeve when in place on the wearer's leg. It will be appreciated that the sleeve may be inverted for use on the other leg or may be inverted on either leg if the force to be applied to the patella is medial and/or upward.

A glide 14 cooperates with the sleeve to provide force vectors to the patella, the glide being generally illustrated as U-shaped, consisting of a bight 30 and generally parallel extending legs 31 and 32. Preferably at least portions of the legs of the glide are formed of an elastomaric material, and generally of a material having a greater maximum resilient strength than that of the sleeve as the legs will be placed under tension. In a preferred embodiment, a firm Neoprene or other synthetic rubber may be used for the glide or at least the leg portions thereof.

A pad 15 is carried by the glide 14 projecting from an undersurface 33. The pad 15 is again preferably U-shaped or C-shaped with one extended leg, having a bight 40 and upper 41 and lower 42 legs. The legs 41 and 42 overlie the undersurface of the legs 31 and 32 spaced from the ends 34. Preferably the upper leg 41 is longer than the lower leg 42 and the space between the legs is chosen to create an inside bight area 44 dimensioned to engage and partially cup the lateral surface of the skin covered patella. As the patella itself generally has a rounded lateral edge, the cross section shape of the pad 15 may have a somewhat rounded or concave inner surface 18 whereby a superior portion 19 of the pad may conform to the rounded superolateral surface of the patella at least above the principal axis of the patella. To facilitate nestling of the patella with respect to the pad, the pad will preferably have a thickness greater than one half the thickness of the patella adjacent its superolateral edges such that the boundary regions of the patella can be received partially within the innermost boundary of the pad.

The longer leg 41 continues along inside surface of the pad and will overlie the superior surface of the patella at least for a portion of the width of the patella whereby in addition to medial force vectors from the bight area of the pad 15, more vertically oriented force vectors can be applied to the top of the patella. The pad 15 may be formed as a separate part of the glide and affixed to the leg portions 31 or may be an integrated portion. The pad portion has a thickness greater than the thickness of the legs and is formed of, or filled with, a yieldable or displaceable material, such as silicon or other gels, which will allow the surfaces of the pad contacting the skin at the patella to generally conform to the shape of the patella in the area of force application. Although many different construction techniques will be apparent to those of ordinary skill in the art, the pad can be formed as a bladder portion of the glide and filled with a fluid with at least portions of the bladder wall being elastic. In other constructions the pad can be separately formed and adhered to an undersurface portion of a U-shaped glide base. In other forms the pad may be formed as a separate body forming at least portions of the bight of the glide and adhered to elastic leg members or straps.

The glide is affixed at the bight end to the sleeve adjacent the lateral side of the opening 25. As illustrated, in order to allow for maximum positioning of the glide, a tab 50 may be affixed to project from the outer surface of the glide, with the tab securely fastened, at least at its outer portions to the sleeve. The use of a tab allows pivoting movement of the glide with respect to the sleeve. While various forms of attachment will be apparent, including thermal bonding, adhesives, stapling, riveting or the like, in a preferred embodiment the tab may be stitched to the sleeve as stitching can facilitate a range of movement between the sleeve and the glide. Although the preferred embodiment illustrates only one such tab 50, it will be apparent that others can be utilized, however it is desired that the attachment of the glide to the sleeve accommodate pivotal movement of the glide with respect to the sleeve, at least to the extent desirable to secure an appropriate degree of contact between the upper leg 41 and superior surfaces of the skin covered patella.

Fasteners 52, 36 are provided for attaching the legs to the sleeve with the legs 31 and 32 under varying degrees of tensions. Preferred fasteners include hook and loop fasteners 36, 52 engagingly secured both to the outer surface of the sleeve in the areas of the sleeve which will underlie the legs and to the undersurface of the legs. The portions of the fastener attached to the sleeve should allow both medial and vertical tensioning of the legs. Either a plurality of attachment parts may be separately carried by the brace, or the sleeve carried portion 52 may extend over a vertical extent allowing a range of attachment points. Other forms of fastening allowing for adjustability of the position and tensioning of the legs will be obvious to persons of ordinary skill in the art, such as, by way of example, the use of adjustable position buckles.

It will further be appreciated that wherein this invention has been described utilizing terminology such as lateral and superior, referring to the outer and top sides of the patella area, that in certain instances the patellar malalignment may be otherwise such that the terms medial, inside, lower or bottom may be appropriate for a particular patient's condition.

In use, after the sleeve has been positioned on the leg in the knee area with the patellar area aligned with the opening, the pad will be brought into contact with the appropriate surfaces of the skin over the patella and the leg tension will thereafter be adjusted to provide a proper force vector, as desired for biasing the patella towards proper alignment. A greater or lesser amount of force can be applied by greater or lesser stretching of the legs of the glide and vertical force orientations can be controlled both by adjusting the tension on the legs and by rotation of the glide with respect to the sleeve in the vertical plane. It will be further appreciated that while the pad has been shown in the preferred embodiment as having a "swoosh"-like shape, where the end of at least the upper leg 41, and preferably upper and lower legs 41 and 42 taper together, and where the upper leg is longer than the lower leg, thereby facilitating superolateral forces to enhance realigning properties of the sleeve, other shapes may be chosen as desired.

We claim as my invention:

1. A patellofemoral brace comprising a generally tube shape hollow sleeve member adapted to be received about a patient's leg at, above and below the knee joint, the sleeve being elastic to constrictingly engage at least portions of the user's leg, the sleeve having an opening through a portion thereof adapted to be positioned to expose the patellar area of the leg, at least portions of the sleeve being constructed of a material having a resistance to movement on the skin when under elastic tension, a generally U-shaped glide having a bight portion pivotaly attached to the exterior of the sleeve by an attachment to the sleeve at at least one point adjacent to but spaced from a side of said opening and free end leg portions extending from the bight, the attachment to the sleeve allowing the glide to pivot with respect to the sleeve opening superiorly and inferiorly, the glide bight area having a least an inside face thereof contacting a conformable displaceable material pad, the pad being generally U-shaped having a bight with extending legs with one leg of the pad extending along an undersurface of one of said glide leg portions for a portion of said one leg portion's distance to an extent greater than an extent of said pad's other leg's extension along the other of said glide leg portions, at least portions of the glide leg portions being elastic, at least one second fastener secured to the sleeve exterior selectively removably securing each of the glide leg portions to the sleeve under tension at points remote from the attachment of the glide bight to the sleeve, the glide leg portions having mating third and fourth fasteners adjacent respective free ends of the leg portions for removably and separable securing the leg portion to the sleeve second fasteners, the fasteners allowing variable positioning of the pad and variable tensioning of the legs to bias the pad towards the patella along selected differing vectors.

2. The brace of claim 1 wherein the pad has a skin facing inner surfaces, an external facing outer surface a thickness between the surfaces, a contact surface positioned between the inner and outer surfaces having a length for contacting the skin of a user at the patella, the contact surface having a face having a free state at least having a generally concave shape for at least a portion of its length whereby the pad contact surface face in its free state has an innermost portion partially overlying an upper surface portion of the skin covered patella while portions of the face contact a peripheral edge surface of the skin covered patella outwardly of the innermost overlying portion.

3. A patellofemoral brace comprising a generally tube shape hollow sleeve member adapted to be received about a patient's leg at, above and below the knee joint, the sleeve having an anterior face with an opening therethrough for exposing the patellar area of the knee and a posterior section, the posterior section having an axial height less than an axial height of the anterior face, the sleeve being elastic to constrictingly engage at least portions of the user's leg, the posterior portion having at least an interior surface thereof formed at least in part of a woven or non-woven fabric, an adjustable glide pivotally secured to said sleeve exterior of the sleeve at one of a lateral or medial side of said opening at a position spaced from the opening, the glide contacting a pad at least partially overlying at least one of the lateral or medial sides of the anterior opening and including spaced superior and inferior legs extending away from the at least one of the lateral and medial sides, at least portions of the legs being elastic, interengaging fasters carried by each of the legs and the sleeve exterior providing for adjustable attachment of the legs to the sleeve at points sufficiently spaced from the pad to apply an elastic bias to the pad, the pad having a contact surface for contacting the skin at the periphery of the patella when the sleeve is positioned on the leg, tensioning of the glide straps being variable to apply differently directed force vectors from the pad to the patella, the pad formed of a displaceable material having resistance to displacement, the pad having an inside face extending between a pad top facing away from the patient's leg and a pad bottom facing the patient's leg when the brace is in position on a patient's leg, the inside face having a generally free form shape which is generally concavely shaped between pad top to pad bottom forming a contact surface to contact both at least one of a lateral or medial side of the skin covered patella and at least one of a superior or inferior side of the skin covered patella.

4. The brace of claim 3 wherein the pad material is a silicon which resists sliding on the patient's skin.

5. The brace of claim 4 wherein the contact surface of the pad has a inside-to-outside extent which is concavely configured, in a free state, to approximate the configuration of the area of the patella to which force is to be applied by the pad whereby a portion of the patella boundary is nestled within the contact surface.

6. The brace of claim 5 wherein the sleeve has at least portions thereof formed of neoprene.

7. The brace of claim 6 wherein the fasteners on the legs and the sleeve are hook and loop fasteners.

8. The brace of claim 7 wherein the glide is substantially U-shaped with the pad positioned at the inside of the bight and extending along at least one leg for a distance greater than any extension of the pad along the other leg whereby a force vector applied to the patella will be one of medially and inferiorly or laterally and superiorly.

9. A patellofemoral brace comprising a generally tube shape hollow sleeve member having an interior and an exterior and adapted to be received about a patient's leg at, above and below the knee joint, the sleeve being elastic to constrictingly engage at portions of the user's leg, the sleeve having an opening through an anterior portion thereof adapted to be positioned to expose the patellar area of the leg, a glide secured to the sleeve exterior laterally of the anterior opening, the glide being pivotal in superior and inferior directions with respect to the anterior opening, the glide being substantially U-shaped having a bight area partially overlying lateral portions of the opening and spaced superior and inferior legs extending from the bight area, the legs having at least portions thereof formed of elastic material, a pad positioned at the bight and at least along a portion of the superior and inferior legs, the pad having a thickness from an inside surface facing towards the interior of the sleeve to an outside surface facing the away from the interior and being bounded at at least portions of an inner periphery of the pad overlying the opening by a contact surface extending from adjacent the interior surface to adjacent the exterior surface, the contact surface having a free state depressed configuration extending inwardly into the pad whereby portions of outer surface of the pad facing away from the interior of the sleeve at the contact surface extends at least centrally of the opening to an extent greater than portions of the pad at the contact surface positioned closer to the sleeve, the depressed surface configuration adapted to assist the pad in conforming to a pad contacted area of a skin covered patella positioned in the anterior opening, fasteners carried by the legs, second fasteners carried by the sleeve exterior medially of the pad, the fasteners of the legs and the sleeve being selectively engageable and disengageable with at least one of the legs under tension when engaged to urge the pad into contact with the skin covered patella to bias the pad towards the patella with a force vector, the force vector being variable in both direction and strength by selective adjustment of the engagement of the leg and sleeve fasteners.

10. The brace of claim 9 wherein the pad is formed of a resilient deformable material.

11. The brace of claim 10 wherein the pad extends along one of the legs from the bight a distance greater than an extent of the pad along the other of the legs from the bight.

12. The brace of claim 11 wherein the depressed configuration of the contact surface of the pad continues at least partially along the extent of the pad along the leg having the longer extension of the pad.

\* \* \* \* \*